United States Patent [19]
Wood

[11] Patent Number: 5,852,308
[45] Date of Patent: Dec. 22, 1998

[54] MICROMACHINED INFERENTIAL OPTO-THERMAL GAS SENSOR

[75] Inventor: R. Andrew Wood, Bloomington, Minn.

[73] Assignee: Honeywell Inc., Minneapolis, Minn.

[21] Appl. No.: 884,824

[22] Filed: Jun. 30, 1997

[51] Int. Cl.$^6$ .................................................. H01L 23/58
[52] U.S. Cl. .......................... 257/252; 257/253; 257/414; 250/343; 73/31.06
[58] Field of Search ..................................... 257/414, 252, 257/253, 467, 81; 250/343, 339.06, 339.13, 345; 73/204.26, 31.06

[56] References Cited

U.S. PATENT DOCUMENTS

| | | | |
|---|---|---|---|
| 5,444,249 | 8/1995 | Wong | 250/343 |
| 5,468,962 | 11/1995 | Ohishi et al. | 250/343 |
| 5,600,148 | 2/1997 | Cole et al. | 250/495.1 |
| 5,616,826 | 4/1997 | Pellaux et al. | 73/24.02 |
| 5,650,624 | 7/1997 | Wong | 250/338.5 |
| 5,668,376 | 9/1997 | Weckström et al. | 250/495.1 |
| 5,747,808 | 5/1998 | Wong | 250/343 |

FOREIGN PATENT DOCUMENTS

| | | |
|---|---|---|
| 4116280 | 12/1991 | Germany . |
| 4208135 | 9/1993 | Germany . |
| 4224518 | 1/1994 | Germany . |
| 1352977 | 5/1974 | United Kingdom . |

Primary Examiner—William Mintel
Attorney, Agent, or Firm—John G. Shudy, Jr.

[57] ABSTRACT

A micromachined integrated opto-thermal sensor having a rapidly intensity varying or pulsing light source, an interference filter, shadow masking or reflective blocking of light from thermal sensors, or differential operation, a gas cavity into which the detected gas can flow into via a channel or filter, and a thermal detector elements to sense the heating of the gas caused by the absorption of light at a particular wavelength by the specific gas to be detected. Another version of the sensor is one with a dual cavity. One cavity contains the gas to be detected and the other cavity is sealed from the ambient environment and contains no gas. Signals from the detectors from the cavities are subtracted from each other resulting in the elimination of a fixed signal due to radiation impinging the detectors. A ratio of the signal from the detectors may be calculated for determining a presence of gas or fluid. The detector may have only a single cavity with two groups of thermal sensors. Each group of sensors receives radiation filtered by an interference filter which passes radiation of one wavelength for one group and of another wavelength for the other group. A ratio of the resultant signals from the two groups of thermal sensors, respectively, is calculated to determine the presence of gas in the near ambient environment of the detector.

45 Claims, 6 Drawing Sheets

MICROMACHINED INFERENTIAL OPTO-THERMAL GAS SENSOR

BACKGROUND

The invention pertains to gas sensors and particularly to toxic gas sensors. More particularly, the invention pertains to micromachined integrated circuit gas and fluid sensors.

Related art devices for sensing toxic gases such as CO, $CO_2$, NO, $NO_2$ and VOCs generated by combustion processes have been based on sensors indicating changes in metal oxide film conductivity, chemiluminescence, fluorescence, various forms of IR absorption, and so forth. These sensors have been too costly, unstable, or insensitive to meet the requirements of a low-cost, reliable toxic gas sensor. Their sensing such toxic gases in concentrations that are commensurate with the levels at which they can be harmful to health and life is difficult, especially if it is to be done via low-cost, affordable and reliable sensors. Often the older gas engines or heaters, operated by budget-minded users, are most likely to be a source of toxic gases that endanger these users and others. These users are the ones most unlikely to buy toxic gas indicators, unless someone manages to bring affordable and appropriate technology to them.

Optoacoustic gas sensors sense low concentrations of gases by inducing a gas temperature variation by narrow-band modulated illumination at a wavelength which the gas absorbs. The modulated temperature signal is not sensed directly, but a closed or nearly closed gas sample cell is used which converts the small gas temperature signals into a pressure signal, which is detected by a microphone. A closed or nearly closed gas cell makes it difficult for gas to enter and exit the gas cell.

SUMMARY OF THE INVENTION

Direct sensing of the gas temperature modulation signal, which is called optothermal sensing, removes the need for a closed or nearly closed gas cell. The direct sensing of the gas temperature signal is handicapped by a lack of a suitably sensitive (i.e., nanodegree sensitivity) and fast-response gas temperature sensor. The use of a micromachined thermoelectric sensor array does allow suitably sensitive, fast response detection of the small gas temperature modulation signal. Such arrays are conveniently fabricated by silicon micromachining.

The present invention provides a new, useful, low-cost and reliable direct sensing of the gas temperature signal of the present gas, and also provides the inferred indication of the presence of a toxic gas or objectionable constituents of combustion products. It is not necessary to directly measure the toxic or objectionable gases, if one can identify a phenomenon that would indicate or infer their presence with a meaningful probability level. The present sensor thus provides more compact, reliable, affordable detection than direct NDIR sensing of toxic gases. It also provides additional detection/alarm protection against high $CO_2$ or other gas concentrations by direct sensing.

The sensor takes advantage of the indirect indication of toxic combustion products, such as CO, $NO_x$ and VOCs via $CO_2$ detection, and a low-cost, integrated gas sensor design is thus made available at a reasonable price to meet the toxic gas sensing needs of users of unvented space heaters (or kitchen stoves) and the needs of automobile drivers that wish to detect exhaust fumes from cars or near them.

Carbon dioxide ($CO_2$) indicates the presence of objectionable concentrations of combustion products. $CO_2$ i generated by combustion processes, in concentrations that are 10 to 100 times higher than those of CO, $NO_x$ or VOCs are. Yet one can measure $CO_2$ at concentration levels that are 3 to 30 times lower than the above-noted gases, especially via NDIR. Combustion products, especially those from gasoline or diesel fuel are known to consist of 5–15% $CO_2$, 10–20% $H_2$, 0–10% $O_2$, 70–80% $N_2$, 0.001 to 0.4% $NO_x$, 0.001 to 0.2% CO (CO in worn or maladjusted automotive engines may be up to 2%), and 0.001 to 0.3% hydrocarbons (HC), i.e., $CO_2$ concentrations always predominate. Still, dilution of exhaust gas of the car in front is expected to be 10 to 1000-fold before reaching the cabin air intake of the following car, so that the $CO_2$ concentration is likely to be only 0.005 to 1.5 %, which is measurable, while the toxic gas concentration is in the 0.0001 to 0.04% range. The latter concentrations are much more difficult to measure, and especially so with low-cost sensors, which would often not begin to sense those gases in spite of being present in concentrations that cause discomfort or adverse health effects.

The integrated design of the present sensor enhances its manufacturability and affordability. The gas cell, thermal detector and optical filter are integrated into one compact micromachined unit which is of lower cost, i.e., more affordable and more widely applicable than higher cost sensors. Infrared radiation may be obtained from small light bulbs, or from electrically heated microbridges (microemitters). Electronic circuits may also be integrated into the silicon material. The sensors are more compact and therefore more rugged, and overall more useful. The integrated opto-thermal sensor used as the detector of the present gas results in a more sensitive, faster response and more stable detection. The faster response is because a closed or nearly closed gas cell is not required.

The integrated sensor is 10 to 100 times smaller than the related art sensors, which makes the present system more affordable, portable and useful. The present detectors are also 10 to 100 times less costly than the related-art detectors because they can be mass-produced using silicon micromachining.

The present highly accurate gas detector is formed from micromachined silicon technology thereby being much smaller than related-art detectors.

In summary, the invention is a low-cost opto-thermal sensing system, which is a micromachined integrated sensor, which has a pulsing, heated radiation source, an appropriate multi-layer interference filter (IF), anti-reflective (AR) film, shadow masking or reflective blocking to prevent light from impinging thermal sensors, and specially etched silicon wafer or masking designed to maximize the infrared red (IR) or light of other wavelengths, to provide energy efficiency at, for instance the 4.3 micron wavelength band of $CO_2$, a sample gas cavity into which gas can flow in and out via channels, or diffuse in and out the etch holes used earlier in fabrication to dissolve the sacrificial layer utilized to form the cavity or via a porous compressed stainless steel frit, and a micromachined gas temperature sensor, operated in single-output or differential-output manner.

The effect of slow ambient temperature variations on the sensor is naturally rejected by a thermoelectric junction-pair arrangement. The effect of gas temperature variations caused by air and/or gas drafts may be minimized by suitable porous baffles, and by lock-in detection. To minimize background signals, the thermoelectric temperature sensors may be not directly illuminated by the optical radiation, and may be coated with a reflective material, and may be operated in a differential manner by placing suitable IFs between the optical illuminator and the gas temperature sensors, and a suitable gas inlet arrangement.

A version of the sensor is one with a dual cavity. One cavity contains the gas to be detected and the other cavity is sealed from the ambient environment and contains no gas. Signals from the detectors from the cavities are subtracted from each other resulting in the elimination of a fixed signal due to radiation impinging the detectors.

DESCRIPTION OF THE EMBODIMENTS

Figure 1:
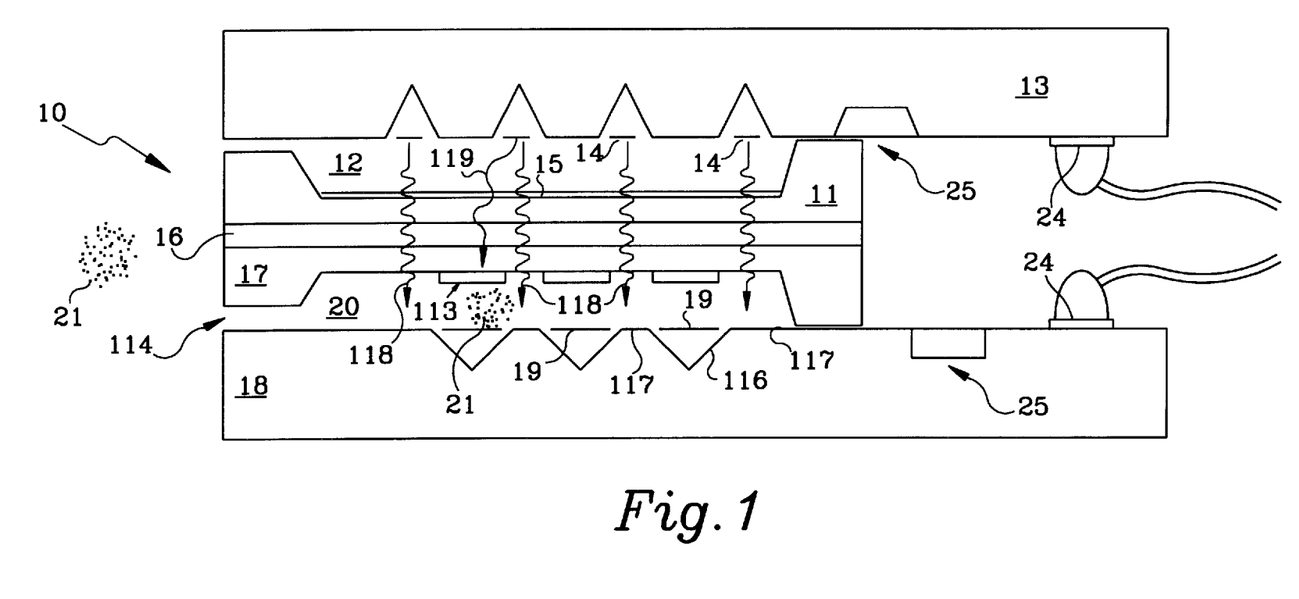
FIG. 1 shows a micromachined inferential opto-thermal gas sensor.

FIG. 1 is a diagram that shows a basic structure of inferential opto-thermal gas sensor 10. Silicon wafer 11 has an etched space 12 on one side. On that side having depression 12 is formed a silicon wafer 13 having a set of microemitters 14 on the side adjacent to wafer 11. Formed on the surface or side of wafer 11 adjacent to microemitters 14 is an antireflective (AR) coating 15. On the other side of wafer 11 is a narrow band pass interference filter (IF) 16 designed to pass only infrared light having a wavelength that is the same as the absorption wavelength (4.3microns) of $CO_2$. The AR and IF coatings or films may be interchanged in location with each other. Silicon wafer 17 is formed on filter 16. Silicon wafer 18 is formed on wafer 17. Silicon wafers 17 and 18 are etched to form a cavity 20 and channels 114. Channels 114 form a pathway between cavity 20 and the ambient volume or space external to sensor 10. Gas or air 21 can diffuse or flow in and out of cavity 20 via orifice, path or channels 114. Wafer 18 has thermal sensors 19 formed over pits 116. Microemitters 14 and thermal sensors 19 are connected to contact pads 24. Formed on wafer 13 or 18 may be an integrated circuit (IC) or an application specific integrated circuit (ASIC) for providing electronics 25 for controlling microemitters 14 or processing signals from thermal sensors 19. Wafer 11 may be substituted with a glass plate. Even wafer 17 may be substituted with glass. In the embodiments disclosed below, the IF filter and the AR coating may be situated or formed on glass, also.

Radiation source 14 is a 32 ×32 array of microemitters that function as an infrared radiation source. Array 14 provides total emission at 4.3 microns about 2.8 times that of a mini-tungsten light bulb. Cavity 20 is about 100 microns deep ×500 microns wide. Cavity 20 cannot be too small or gas cooling at cavity surfaces would reduce the sensitivity of gas sensor 10.

The thermal sensor is a 64 ×64 array of series-connected NiFe:Cr thermoelectric sensors 19, each having two thermoelectric metallic junctions per each 50 micron ×50 micron silicon nitride microbridge, one junction on the microbridge and one on the adjacent silicon, with 10 ohms resistance per junction-pair, and a junction pair Seebeck coefficient of 60 microvolts/degree C. The thermoelectric sensors 19 are coated with a reflective metal layer to minimize direct absorption of infrared radiation. The thermal sensor has a typical microbridge response time of 0.5 millisecond and a 10 Hz illumination modulation. The lock-in electronics detection system (for example, amplifier 102, power source 104 and lock-in amplifier 103 in FIG. 3 with source elements 94 instead of lamp 93) has a 30 second response time (i.e., bandwidth dF =0.02 Hz). The rms voltage noise =square root of (4 KT(64 ×64)RdF) =2.5 nanovolt rms/ and sensitivity=(2.5e−9)/(64 ×64×60e−6)=10 nanodegree C. rms. This allows detection of typical gas temperature signals from a $CO_2$ concentration of about 100 ppm.

In FIG. 1, source 14 emits light 118 and 119. Light 119 is blocked by shadow masks 113. Light 118 goes through layer 15 and wafer 11. Only light 118 having a wavelength that is passed by narrow band pass interference filter 16 enters cavity 20 and is able to impinge air and/or gas 21 molecules. If such gas 21 has an absorption wavelength that is the same wavelength of light 118 that passes through filter 16 and impinges gas 21, then that light 118 is absorbed by gas 21 and gas 21 heats up. The increase of the temperature of gas 21 is sensed by thermal sensors 19, which output signals indicative of the presence of gas 21. Light 118 that is not absorbed by gas 21 impinges non-thermal areas 117 and does not affect sensors 19. Little light 118 or 119 will hit sensors 19 because of shadow masks 113. Light 119 from source 14 passes through film 15, wafer 11 and narrow band pass filter 16, and impinges masks 113. Masks 113 largely block light 119 that would otherwise enter cavity 20 and impinge thermal sensors 19. Impingement of sensors 19 by light 119 would cause sensors 19 to warm up and provide fixed signals not indicating presence of a gas. If light 119 impinged sensors 19, electronics may be used to remove fixed signals caused by such light 119 and pass only true signals indicating the presence of gas 21. This method of operation requires very stable electronics to remove the fixed signals.

Figure 6A:
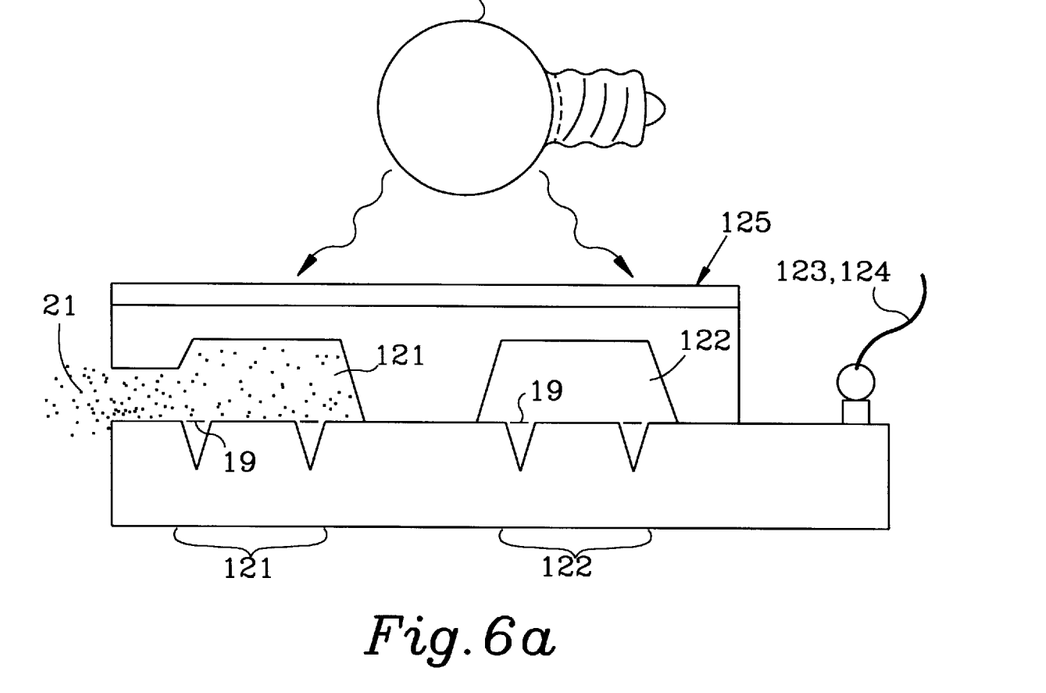
FIGS. 6a, 6b, 6c and 6d show a sensor operation in a differential manner.
Figure 6B:
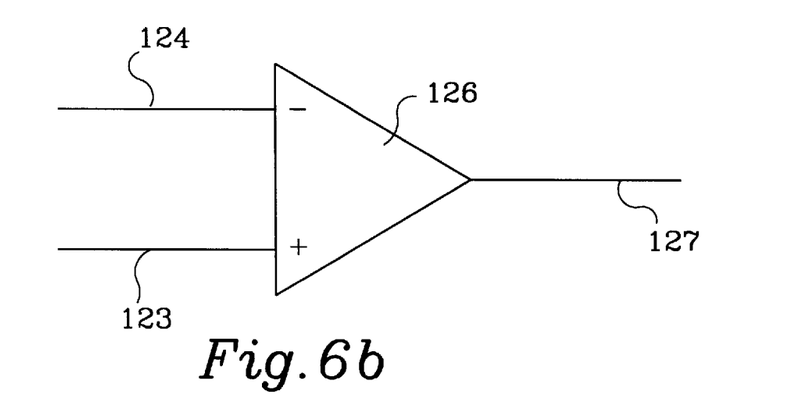

An alternative approach in FIG. 6a is to employ two arrays, 121 and 122, of thermal sensors 19, both illuminated by the same radiation source 120 through infrared filter 125 with one array 121 exposed to gas 21 and the other array 122 not exposed to gas 21. In FIG. 6b, two signals 123 and 124 from two arrays 121 and 122, respectively, may then be electronically subtracted to give a signal 127 by a differential amplifier 126 to substantially remove the fixed signals caused by impingement of thermal sensors or temperature detectors 19 by radiation.

Figure 6C:
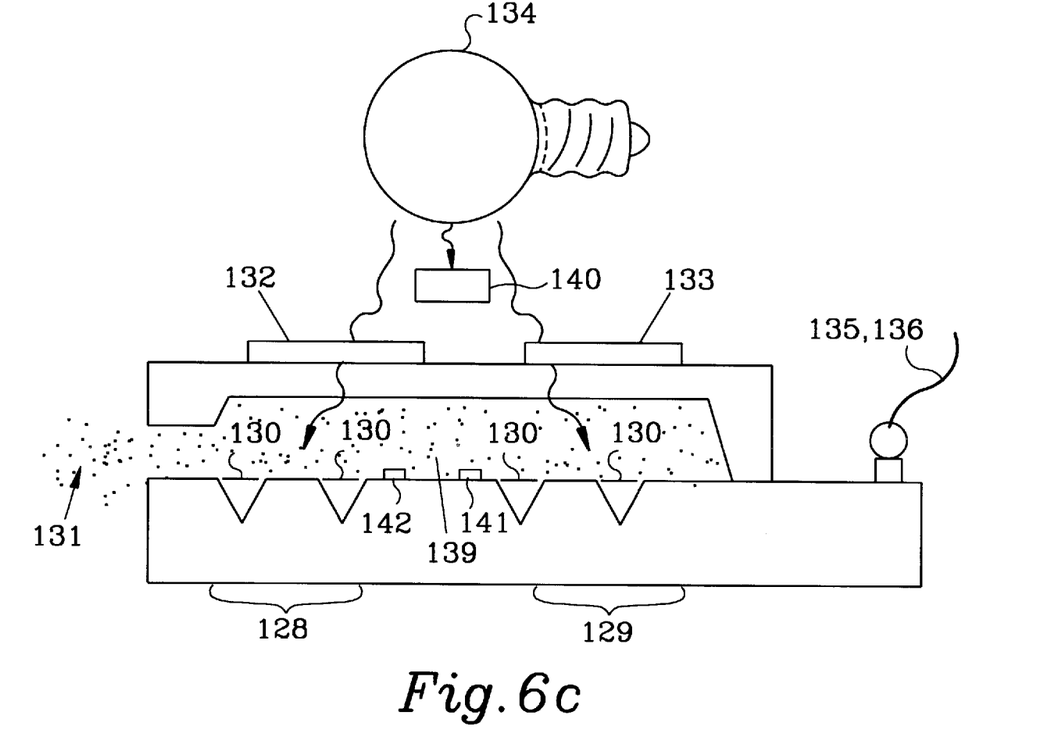
Figure 6D:
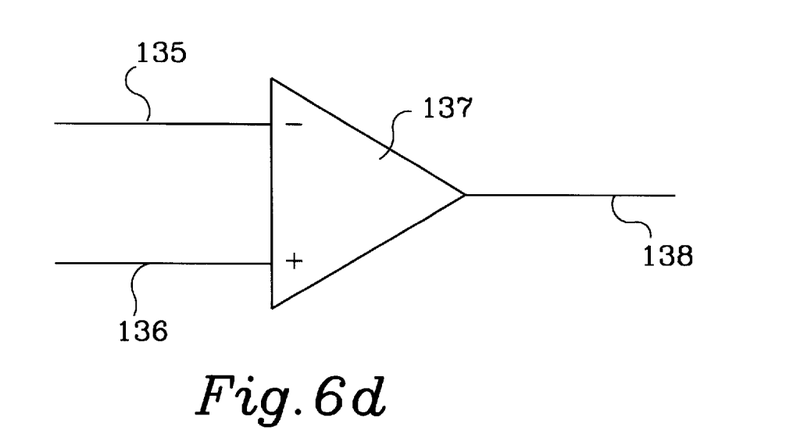

FIG. 6c shows another differential approach, in which two arrays 128 and 129 of thermoelectric sensors 130 in a common gas cavity 139 are illuminated by two different wavelengths obtained by a lamp 134 and two different interference filters 132 and 133, such that the two wavelengths are substantially equal in intensity, but one wavelength is absorbed by the gas 131 to be directly sensed, and the other wavelength is not. A first electrical signal is taken from array 128, comprising a fixed signal caused by impingement and absorption of radiation on sensors 130 together with a signal component dependent upon the concentration of the gas to be directly sensed. A second electrical signal is taken from array 129, comprising only a fixed signal caused by impingement and absorption of radiation on sensors 130. The two signals are taken via leads 136 and 135 respectively, to a differential amplifier 137 shown in FIG. 6(d), producing a subtracted signal 138 in which the fixed signal caused by impingement and absorption of radiation on sensors 130 is substantially removed.

In the differential approaches shown in FIG. 6(a) through (d), the magnitude of the second signal may be used as a measure of the intensity of the radiation source, so that changes in the intensity of the radiation source may be detected and the signals corrected accordingly.

The configuration of FIG. 6c compensates for changes in the thermal conductivity of the gas in cavity 139. Such thermal conductivity changes do in fact change both the first and second signals, but this signal change due to gas thermal conductivity is effectively removed by taking the ratio of the first 135 and second 136 signals.

The second signal is an indication of the magnitude of the intensity of radiation source 134 and the thermal conductivity of the gas in the cavity. The gas thermal conductivity will change second signal 136, and thus second signal 136 may not be able to be used to measure radiation source 134 brightness in all circumstances. In such cases, it may be necessary to use a separate photosensor 140 to measure the radiation source 134 brightness. Photosensor 140 provides an indication of the magnitude of the radiation. This provides a way of measuring the source brightness directly, independent of gas thermal conductivity. It also allows a measurement of the gas thermal conductivity, which may be useful in some cases. Photosensor 140, if necessary, can control the drive voltage to keep the brightness constant. Photosensor 140 should be placed so as to be illuminated by radiation source 134. A heater resistor 141 and temperature sensor 142 can be used to maintain the sensor at a fixed temperature. In some circumstances, it may be useful to maintain the sensor at a fixed temperature, which is normally done by heating it slightly to a fixed temperature. This is done so that sensor parameters, which are temperature dependent, do not vary (e.g., the sensitivity of a thermocouple or photosensor may be temperature dependent). Sensors 141 and 142 may be situated on the same surface as that of the thermal sensors.

There is an advantage to measure a ratio 143 of the two signals 135 and 136 from the sensor of FIG. 6c, rather than difference 138. The reason is that if one takes the difference, since the signals are never exactly equal, there inevitably is left some residual signal. This is fine except that the residual signal is dependent on the thermal conductivity of the gases 131 present in the sensor, and thus the presence of a gas of markedly different thermal conductivity will produce a sensor signal indistinguishable from a signal due to the gas species desired to be sensed. On the other hand, ratio 143 of two signals 135 and 136 is much less sensitive to the thermal conductivity of the gases present. This is because the numerator and the denominator vary with gas conductivity very much the same and cancel out in the ratio. Experiments confirm that the ratio works better than the difference, in that the presence of a gas 131 of a different thermal conductivity produces little effect.

FIG. 6c shows the form of the sensor that seems to work well. As shown in FIGS. 6a and 6c, the device can actually be made with one wafer 144, 145 (having micromachined thermal sensors), and a topcap 146, 147. The main purpose of the topcap is to protect the delicate micromachined thermal sensors from dust or draughts. Topcap 146, 147 can be a second silicon wafer, but any IR transparent material is fine. One can use either a glass microscope slide or the IR filters themselves as topcap 146, 147. The purpose of adding third and fourth silicon wafers 11 and 13, like those of FIG. 1, is to provide a replacement for light bulb 120, 134 shown in FIGS. 6a and 6c. This approach does have technical advantages over a light bulb, but is much more difficult to implement.

As in the non-differential and ratio approaches, the thermal sensors used in the differential approach may also be provided with radiation masks, or coated with reflective metal layers, to minimize direct impingement and absorption of infrared radiation.

Figure 2:
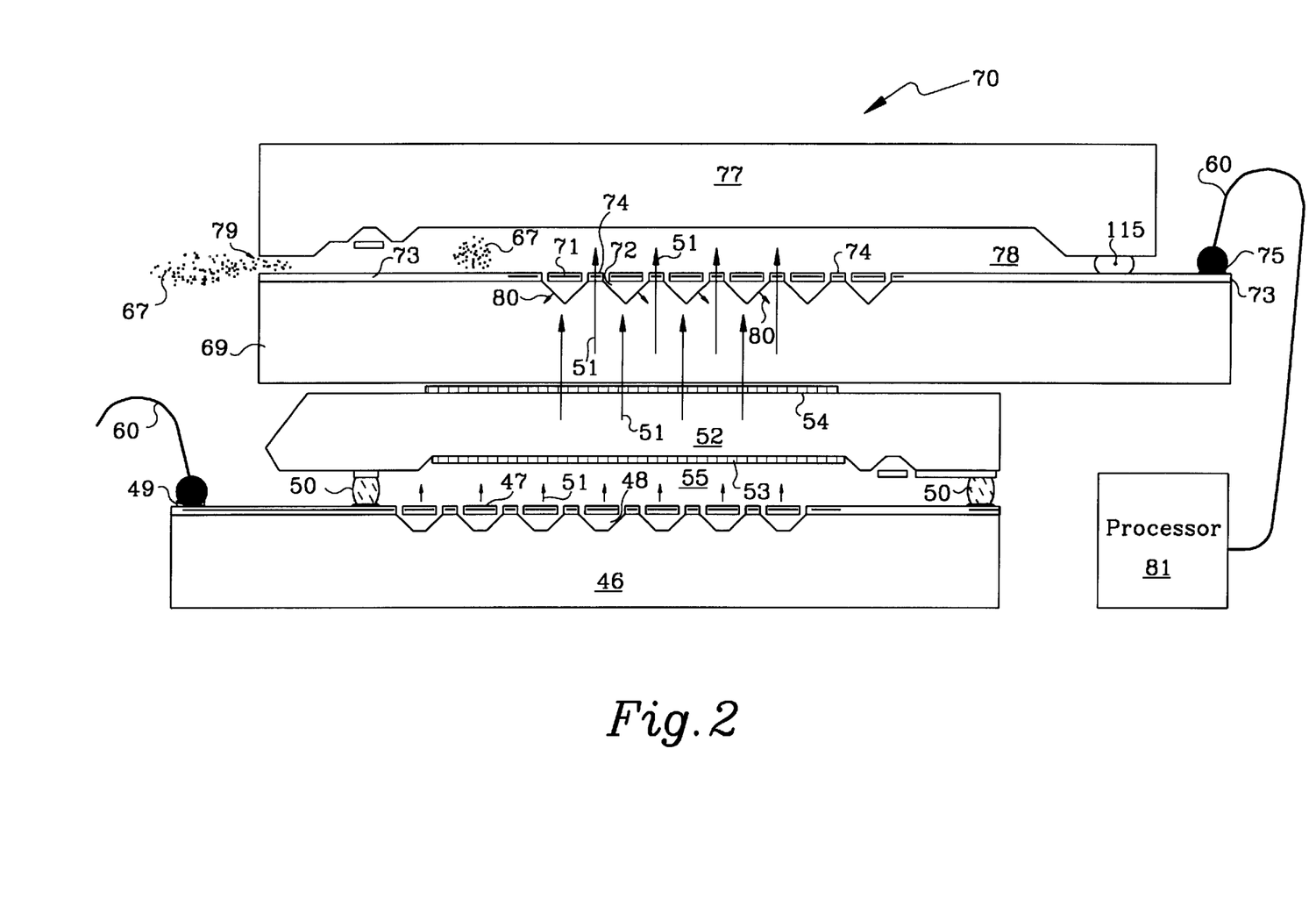
FIG. 2 shows another design of an inferential optothermal gas sensor.

FIG. 2 is a cross-section diagram of an opto-thermal gas sensor 70 with radiation passing in an opposite direction. Silicon wafer 46 is about 5 ×5millimeters (mm) square and about 20 mils thick. Wafer 46 has formed on it a heated radiation source 47 of IR radiation. Source 47 is fabricated from a high refractory material such as silicon nitride with resistive heating materials. Grooves or pits 48 are etched in wafer 46 to minimize heat loss from source 47. Leads 60, about one mil thick, are attached to contacts 49 for providing an AC signal at a frequency from 10 to 100 hertz to activate source 47 so as to emanate radiation 51. Attachment materials 50 are formed on the periphery of chip or wafer 46. A silicon wafer 52 about 20 mils thick is attached in a vacuum, so that space 55 is evacuated of air. An AR film coating 53 is formed on a first side of wafer 52 and a narrow band pass IF multiple stack layer 54 for passing 4.3 microns of light is formed on a second side of wafer 52. AR film layer 53 is about 2 to 6 films of quarter wavelength thicknesses of alternating materials having different indices of refraction. IF layer 54 is a stack of half wavelength films of alternating materials having different indices of refraction. Wafer 52 is brought into proximity with wafer 46 upon contact of attachment materials 50 on wafer 46 at a peripheral surface of wafer 52 to form an evacuated thermally isolating space 55.

The heated radiation source 47, being within 1 to 2 microns of the solid Si substrate, has a fast response, is modulated at as high a frequency as possible (typically 10 to 100 hertz) and fills the cavity with light, which is essential to obtain high sensitivity. If light source 47 were to be an incandescent mini-tungsten filament lamp, the maximum pulse rate of the AC excitation signal would be about 10 hertz. Increased frequency results in better sensitivity since low-frequency electronic noise is less present. The present integrated circuit light source 47 can effectively be cycled or pulsed up to 100 hertz which results in improved sensitivity of sensor 70.

A silicon detector wafer 69 is formed with a first surface on 4.3 micron narrow band pass optical interference filter 54 and silicon wafer 52. Wafer 69 has grooves or pits 72 formed or etched on a second surface of wafer 69 for reflection of radiation 51 and for improved thermal contact of elements 71 with the gas. A thermo-electric (TE) temperature sensor or detector layer 73 is formed on wafer 69. Temperature sensitive elements 71 are formed over pits 72. Elements 71 are coated with reflective metal to minimize direct absorption of infrared radiation. Temperature insensitive and radiation 51 transparent portions 74 of sensor layer 73 are formed on the non-etched portions of the second surface of wafer 69. Electrical contacts 75 are formed on detector layer 73 for electrical signal transmission to and from layer 73 via leads 60. Attachment materials 115 are formed on the periphery of layer 73 and the second surface of wafer 69. A top cap silicon wafer 77 is formed and attached to form cavity 78. The attachment is such that at one or more vias, channels or holes 79 are formed such that gas and/or air can enter cavity 78.

The functioning of opto-thermal gas sensor 70 includes the emission of fluctuating or pulsing radiation 51 having an IR component. Light 51 goes through AR layer 53 and through wafer 52 to IF layer 54. A portion of light 51 is filtered out by narrow band pass film layer 54 which passes only light having a wavelength of, for example, 4.3 microns (for $CO_2$ detection). Filters with other band pass wavelengths may be used depending upon the type of gas or fluid that is to be detected. The 4.3 micron portion of the light enters wafer 69. Virtually all of light 51 that impinges pits 72 is reflected as light 80. Light 51 that impinges the non-etched portions of the second surface of wafer 69 passes through detector portions 74 into cavity 78. Pits 72 reflect light 51 so that temperature sensitive portions 71 are not affected by heat of the incoming light 51. Air and/or gas 67, such as $CO_2$, flows into and through cavity 78 via channels 79. Light 51 is absorbed by $CO_2$ which heats up and causes sensors 71 to heat up and result in the detection of heat and consequently the presence of $CO_2$, since the wavelength of light 51 and the absorption wavelength of $CO_2$ are the same. As gas 67 passes through and is present in cavity 78, light 51 is fluctuating or pulsing in magnitude or intensity and causing the $CO_2$ of gas 67 to heat and cool. Electrical signals from detector elements 71 go to a processor 81 via contacts 75 and leads 60. Processor 81 determines the presence and the amount of $CO_2$ and inferentially indicates the presence of toxic gases present in the immediate environment of gas sensor 70. Reflected light 80 is kept from sensor elements 71 to minimize fixed signals going to processor 81. A differential arrangement like that of FIGS. 6a, 6b, 6c and 6d may be employed. Alterations of sensor 70 may be made like those to sensor 10 to directly sense other kinds of gases or liquids.

Figure 3:
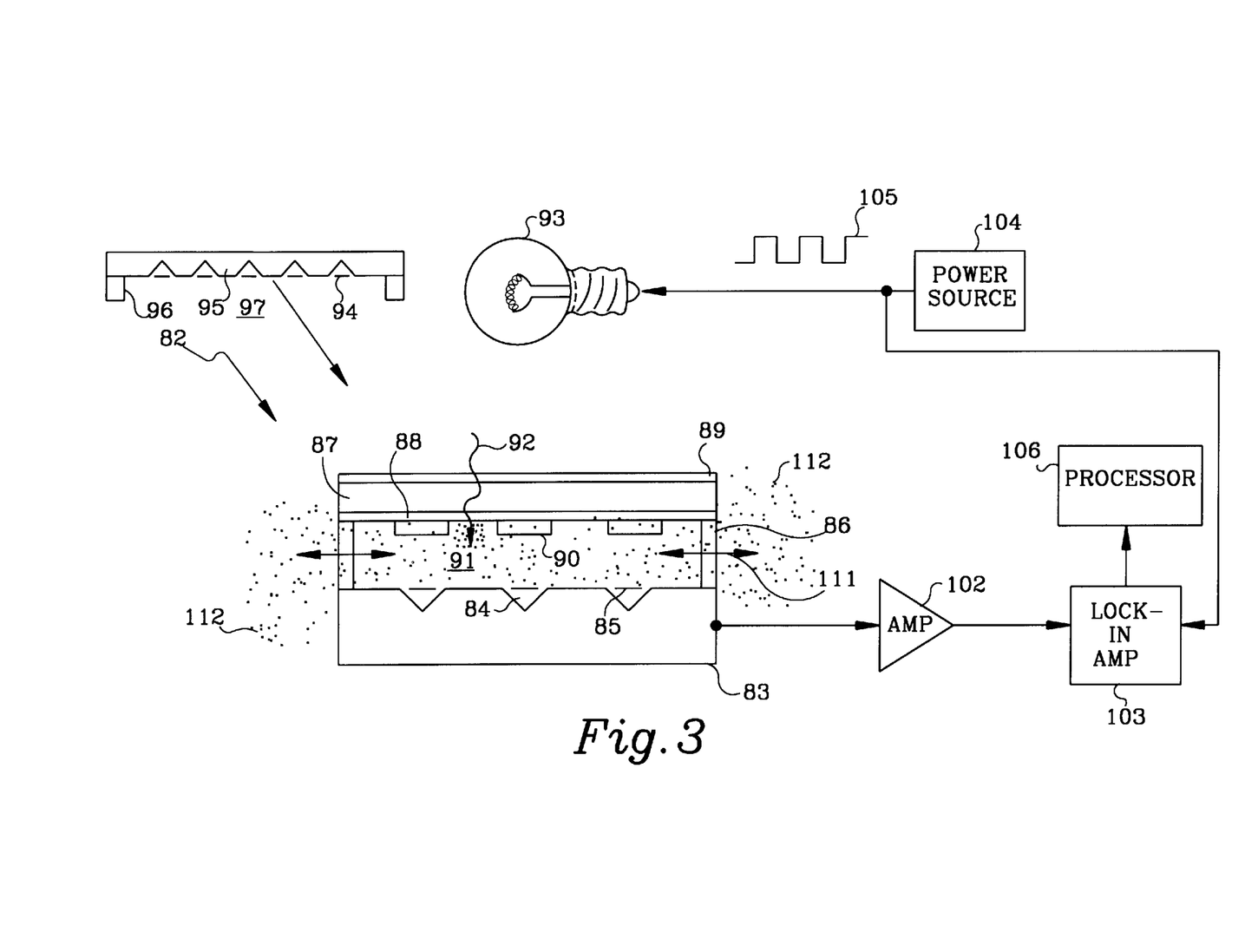
FIG. 3 is of still another design of an opto-thermal gas sensor.

Gas sensor 70 may be designed to directly detect and indicate the presence of other gases or liquids besides $CO_2$. Narrowband pass filter 54 would be changed to a filter that would pass a different wavelength of light 51 which would be equivalent to the absorption wavelength of the other kind of gas to be detected and measured. For instance, filter would be designed to pass 4.6 micron wavelength of light if CO were to be directly detected by sensor 70 or to a wavelength from 3.2 to 3.4 microns if a gas or liquid (VOCs) having hydrocarbon (CH) bonds were to be directly detected by FIG. 3 illustrates another opto-thermal gas sensor 82. A silicon substrate 83 has etched pits 84. Situated over etch pits 84 are thermoelectric receptors 85. Situated on substrate 83 are spacers 86. On spacers 86 is a silicon substrate 87. Formed on one surface of substrate 87 is a a narrow band pass interference filter 88. Formed on the other planar surface of substrate 87 is anti-reflective film 89. Formed on filter 88 are shadow masks 90 which block incoming light coming through film 89, substrate 87 and filter 88 into cavity 91, but only in areas directly over thermoelectric sensors 85. The purpose of each shadow mask 90 is to largely block light 92 coming into cavity 90 from impinging on sensor elements 85. The source of radiation or light 92 may be from an incandescent light bulb 93 or a microemitter array 94 formed on a source substrate or wafer 95. Spacers 96 may be formed on substrate 87 or film 89 to support substrate or wafer 95 containing light or radiation source elements 94. Substrate 95 supported by spacers 96, when formed on wafer 87 or film 89, results in a thermal isolation cavity between wafer 95 and wafer 87 or film 89.

Light 92 from either microemitters 94 or light bulb 93, is modulated with a varying intensity or a pulse waveform. Light 92 goes through thermal isolation cavity 97 if microemitters 94 are used, or initially goes through antireflective film 89 if light bulb 93 is used. After light 92 goes through film 89, substrate 87 and interference filter 88, it enters cavity 91. Light 92 having wavelengths other than the absorption wavelength of the gas to be detected is blocked by narrow band pass filter 88. Light of all wavelengths is blocked by shadow mask 90 to reduce impingement of light 92 on thermal sensors 85. Thermal sensors 85 may be coated with a reflective metal layer to minimize direct absorption of infrared radiation. Air and/or gas 112 of the ambient environment about sensor 82 is free to have a flow 111 in and out of cavity 91. If gas 112 having an absorption wavelength that is the same as the wavelength of light 92 that passes through filter 88, then light 92 is absorbed by that gas 112 and as a result heats up. The increase of temperature of gas 112 is detected by thermal sensors 85. If there is no gas having an absorption wavelength which is the same as the wavelength of light 92 passing through filter 88, then there is no absorption of the light by the gas and no increase or change of the temperature of the gas and/or air within cavity 91. Therefore, thermal sensors 85 detect no change in temperature. However, if shadow masks 90 were not present, then light 92 would impinge thermal sensors 85 which would detect increases and/or changes in temperature in cavity 91, thereby providing a large fixed signal in addition to the gas-dependent signal.

Figure 4A:
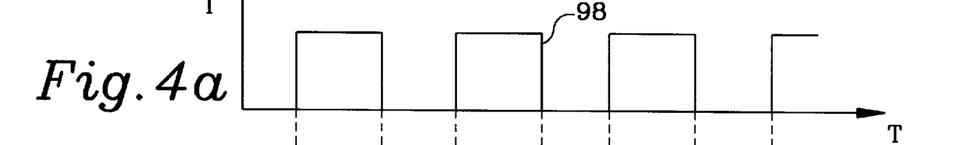
FIGS. 4a, 4band 4care waveform diagrams of light and heat signals of a thermal sensor.
Figure 4B:
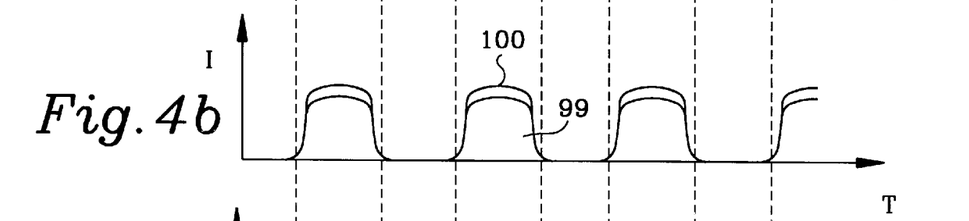
Figure 4C:
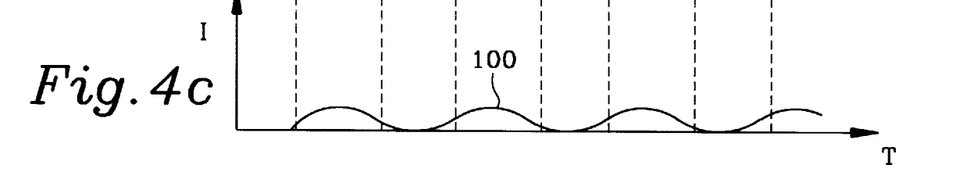

FIGS. 4a, 4b and 4c illustrate the effects of light 92 in cavity 91 with and without shadow mask 90 and metal reflective layers. Waveform of FIG. 4a reveals the amplitude of light 92 coming through filter 88 into chamber 91. FIG. 4b shows a signal 99 from thermal sensor 85 when shadow mask 90 is not present. If there is a gas in chamber 91 having an absorption wavelength, which is the same as that of the light 92 passing through interference filter 88, then increased heat in the chamber as a result of the absorption of light 92 by the gas being detected is superimposed as curve 100 on curve 99. With the shadow mask 90 in place, and with a reflective layer, signal 99 is largely removed due to the blocking of light 92 from impinging on and being absorbed by thermal sensors 85. The resultant sensor signal with sensor 85 isolation from light 92, results in signal 100 shown in FIG. 4c.

Signals from sensors 85 go to amplifier 102 and onto a lock-in amplifier 103. Power source 104 outputs an electrical signal 105 that is provided to light bulb 93 or microemitters 94 to result in light 92 of a pulsed or varying intensity. Also, signal 105 is fed to lock-in amplifier 103. A signal output of lock-in amplifier 103 provides an indication of the amount of concentration of the gas detected in cavity 91 and about the ambient environment of sensor 82. The signal from amplifier 103 goes to processor 106 which inferentially determines from the amount of a directly detected gas, for example, $CO_2$, the presence and amounts of various toxic gases that are in the ambient environment immediately around and about the micromachined inferential toxic gas indicator 82. Processor 106 also infers present or past chemical or physical activity around sensor 82. It also may portend future chemical or physical activity. Processor 106 may have a table of information that indicates certain amounts of concentrations of particular gases or fluids that infer the presence of certain amounts of concentrations of other gases or fluids. The presence of certain amounts of concentrations of other gases or fluids are more accurately inferred by the presence of certain amounts of concentrations of the particular gases or fluids in cavity 91 because the amounts of the detected concentrations, such as $CO_2$, are up to several magnitudes larger than the certain amounts of concentrations of the other inferred gases or fluids.

Figure 5:
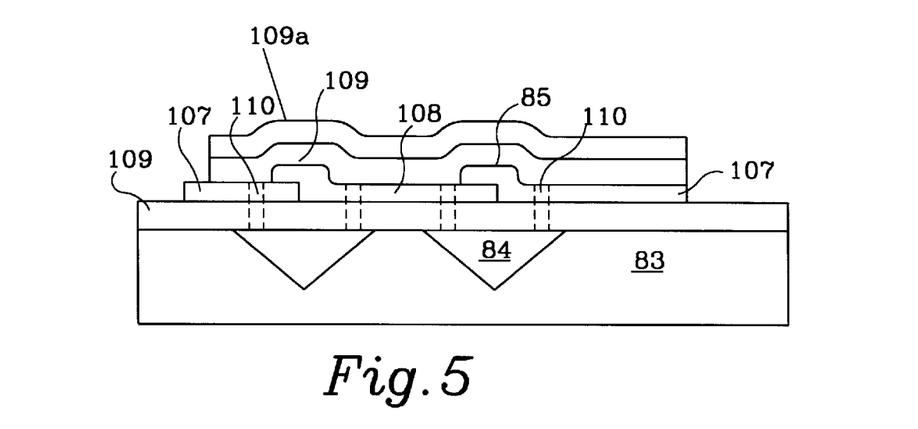
FIG. 5 is a diagram of the structure of a thermal sensor element.

FIG. 5 shows the fabrication of thermo-electric sensor 85. Silicon substrate 83 has an edge pit 84 for purposes of thermal isolation of detector 85. A micromachined array of thermal electric sensors 85 are formed from overlapping thin film metals 107 and 108. They are formed between layers of silicon nitride 109 that is formed on silicon substrate 83. The sensor portion of metal layers 107 and 108 are isolated to the areas of overlap and contact between metals 107 and 108, that are situated over etch pits 84, which cuts 110 define. A metal reflective layer (gold) may be applied (109*a*) to reduce direct absorption of radiation by the thermo-electric sensor 85.

I claim:

1. A dual cavity gas/fluid sensor comprising:
   a first wafer;
   a radiation source formed on said first wafer;
   a second wafer formed on said first wafer;
   a radiation filter formed on said second wafer;
   a third wafer formed on said radiation filter;
   a temperature detector formed on said third wafer; and
   a fourth wafer formed on said temperature detector; and
   wherein:
   said third wafer comprises a radiation mask; and
   said fourth wafer forms first and second cavities over said temperature detector.

2. The sensor of claim 1 wherein said first, third and fourth wafers are silicon.

3. The sensor of claim 1 wherein said second wafer is glass.

4. The sensor of claim 2 wherein:
   said radiation filter is a narrow band pass filter for passing radiation having a first wavelength;
   a gas or fluid to be sensed has an absorption wavelength at the first wavelength;
   the first cavity has at least one orifice so that a gas or fluid in an ambient environment about the sensor can enter into and exit from the cavity;
   the second cavity is sealed from the ambient environment.

5. The sensor of claim 4 wherein:
   said temperature detector comprises a plurality of thermally isolated sensing elements;
   the radiation mask has radiation-blocking areas to prevent radiation from substantially impinging the plurality of thermal sensing elements, and radiation-transmitting areas which permit radiation to heat gas or fluid adjacent to the plurality of sensing elements; and
   radiation that may come from said radiation source and pass through said second wafer, radiation filter, the radiation-transmitting areas of the radiation mask and into the first and second cavities, has an intensity that varies.

6. The sensor of claim 5 wherein the plurality of thermally isolated sensing elements are coated with a reflective layer.

7. The sensor of claim 6 wherein the cavity and the plurality of thermally isolated sensing elements are micromachined.

8. The sensor of claim 7 wherein gas or fluid being in the first cavity and impinged by the radiation from said third wafer, will vary in temperature by a particular amount if the gas or fluid has an absorption wavelength at the first wavelength.

9. The sensor of claim 8 wherein:
   said temperature detector can sense a variation of a temperature of a gas or fluid in the first cavity;
   said temperature detector can output a first signal that indicates a fixed signal component together with a signal indicating a magnitude of the variation of the temperature of the gas or fluid in the first cavity;
   said temperature detector can output a second signal that indicates a magnitude of the variation of the temperature in the second cavity; and
   the magnitude of the second signal indicates the fixed signal component of said first signal.

10. The sensor of claim 9 further comprising a processor, wherein:
    the first signal from said temperature detector in the first cavity, goes to said processor;
    the second signal from said temperature detector in the second cavity, goes to said processor;
    said processor subtracts the second signal from the first signal and outputs a differential signal; and
    said processor uses the second signal to correct for changes in the intensity of the radiation source.

11. The sensor of claim 10 wherein subtraction of the second signal from the first signal removes a fixed signal from the first signal, the fixed signal being due to the radiation impinging on the sensing elements.

12. The sensor of claim 11 wherein said processor processes the differential signal from said temperature detector and provides information indicating the presence of the directly detected gas and inferred information indicative of a presence of other gases or fluids and chemical or physical activity.

13. The sensor of claim 12 wherein the first wavelength is at an absorption wavelength of CO.

14. The sensor of claim 12 wherein the first wavelength is at an absorption wavelength of $CO_2$.

15. The sensor of claim 14 wherein:
    said processor comprises a table of information that indicates certain amounts of concentrations of particular gases or fluids to infer the presence of certain amounts of concentrations of combustion products; and
    the presence of certain amounts of concentrations of combustion products are more accurately inferred by the presence of certain amounts of concentrations of the particular gases or fluids because the latter amounts of concentrations are up to several magnitudes larger than the certain amounts of concentrations of combustion products.

16. The sensor of claim 15 further comprising an integrated circuit formed on said first wafer and wherein said integrated circuit has said processor.

17. The sensor of claim 15 further comprising an integrated circuit formed on said fourth wafer and wherein said integrated circuit has said processor.

18. The sensor of claim 15 further comprising an antireflective coating for the first wavelength formed on said second wafer.

19. A gas/fluid sensor comprising:
    a first wafer;
    a radiation source situated on said first wafer;
    a second wafer situated on said first wafer, said second wafer having a first portion and a second portion;
    a first radiation filter situated on the first portion of said second wafer;
    a second radiation filter situated on the second portion of said second wafer;
    a third wafer situated on said first and second radiation filters;
    a first temperature detector situated on a first portion of said third wafer proximate to the first radiation filter;
    a second temperature detector situated on a second portion of said third wafer proximate to the second radiation filter;

a fourth wafer situated over said first and second temperature detectors; and wherein:

said third wafer has a radiation mask; and said fourth wafer forms a cavity over said first and second temperature detectors.

20. The sensor of claim 19 wherein said first, third and fourth wafers are silicon.

21. The sensor of claim 20 wherein said second wafer is glass.

22. The sensor of claim 19 wherein:

said first radiation filter is a narrow band pass filter for passing radiation having a first wavelength;

said second radiation filter is a narrow band pass filter for passing radiation having a second wavelength;

a gas or fluid to be sensed has an absorption wavelength at the first wavelength; and the cavity has at least one orifice so that a gas or fluid in an ambient environment about the sensor can enter and exit the cavity.

23. The sensor of claim 22 wherein:

said first temperature detector outputs a first signal;

said second temperature detector outputs a second signal;

the first signal has a signal component caused by impingement and absorption of radiation on said first temperature detector and a variable signal component dependent upon a concentration of the gas or fluid in the cavity; and the second signal has a signal component caused by impingement and absorption of radiation on said second temperature detector.

24. The sensor of claim 23 further comprising a differential device having a first input for receiving the first signal, a second input for receiving the second signal and an output for providing a third signal having the second signal subtracted from the first signal.

25. The sensor of claim 24 wherein the second signal is an indication of a magnitude of intensity of said radiation source.

26. The sensor of claim 25, wherein the second signal is an indication of thermal conductivity of the gas or fluid in the cavity.

27. The sensor of claim 26, further comprising a photosensor situated for providing an indication of magnitude of said radiation source.

28. The sensor of claim 27, further comprising:

a heater resistor situated on said third wafer; and a temperature sensor situated on said third wafer; and wherein the heater resistor and temperature sensor are for maintaining the sensor at a fixed temperature.

29. Means for sensing a gas fluid, comprising:

means for providing radiation;

first means for passing radiation at only a first wavelength, proximate to said means for providing radiation;

second means for passing radiation at only a second wavelength, proximate to said means for providing radiation;

means for containing a gas or fluid, proximate to said first and second means for passing radiation;

means for permitting a gas or fluid to enter or leave said means for containing a gas or fluid, proximate to said means for containing a gas or fluid;

first means for detecting temperature of the gas or fluid, proximate to said first means for passing radiation at only a first wavelength; and second means for detecting temperature of the gas or fluid, proximate to said second means for passing radiation at only a second wavelength.

30. The means for sensing a gas or a fluid of claim 29 wherein:

said first means for detecting temperature outputs a first signal;

said second means for detecting temperature outputs a second signal;

the first signal has a fixed signal component caused by impingement and absorption of radiation on said first means for detecting temperature and a variable signal component dependent upon a concentration of the gas or fluid having an absorption wavelength at the first wavelength, in said means for containing a gas or fluid; and the second signal has a fixed signal component caused by impingement and absorption of radiation on said second means for detecting temperature.

31. The means for sensing a gas or a fluid of claim 30, further comprising a means. for providing an output signal that is equivalent to the difference of the first and second signals.

32. The means for sensing a gas or a fluid of claim 31, wherein the output signal indicates a magnitude of concentration of the gas or fluid in said means for containing a gas or fluid.

33. The means for sensing a gas or a fluid of claim 32, further comprising means for reducing direct absorption of radiation by said first and second means for detecting temperature.

34. Means for sensing a gas or a fluid, comprising:

means for providing radiation;

means for passing radiation at only a first wavelength, proximate to said means for providing radiation;

means for containing a gas or fluid having an absorption wavelength at any wavelength;

means for containing a vacuum, or a gas or fluid having an absorption wavelength at a wavelength other than the first wavelength;

first means for detecting temperature, situated in said means for containing a gas or fluid; and second means for detecting temperature, situated in said means for containing a vacuum, or a gas or fluid having an absorption wavelength at a wavelength other than the first wavelength.

35. The means for sensing a gas or a fluid of claim 34, further comprising means for providing movement of gas and/or fluid, external to said means for sensing a gas or a fluid, into and from said means for containing a gas or fluid.

36. The means for sensing a gas or a fluid of claim 35, wherein:

said first means for detecting temperature outputs a first signal;

said second means for detecting temperature outputs a second signal;

the first signal has a fixed signal component caused by impingement and absorption of radiation on said first means for detecting temperature and a variable signal component dependent upon a concentration of the gas or fluid having an absorption wavelength at the first wavelength, in said means for containing a gas or fluid having an absorption wavelength at any wavelength; and the second signal has a fixed signal component caused by impingement and absorption of radiation on said second means for detecting temperature.

37. The means for sensing a gas or a fluid of claim 36, further comprising a means for providing an output signal that is equivalent to the difference of the first and second signals.

38. The means for sensing a gas or a fluid of claim 31 wherein the output signal indicates a magnitude of concentration of the gas or fluid having an absorption wavelength at the first wavelength, in said means for containing a gas or fluid having an absorption wavelength at any wavelength.

39. The means for sensing a gas or a fluid of claim 38, further comprising means for reducing direct absorption of radiation by said first and second means for detecting temperature.

40. A dual cavity gas/fluid sensor comprising:

a first wafer;

a first array of thermal sensors formed on said first wafer;

a second array of thermal sensors formed on said first wafer;

a topcap formed on said wafer so as to result in a first cavity encompassing said first array of thermal sensors and a second cavity encompassing said second array of thermal sensors, wherein said first cavity can receive gas from the ambient environment of the sensor and said second cavity is sealed from the ambient environment; and a radiation source situated proximate to said topcap, for illuminating the first and second cavities.

41. A dual cavity gas/fluid sensor of claim 40, wherein:

said first array of thermal sensors can output a first signal indicative of a presence of a gas or fluid about said first array of thermal sensors;

said second array of thermal sensors can output a second signal indicative of a presence of a gas or fluid about said second array of thermal sensors;

and wherein a ratio is calculated of the first and second signals and said ratio is indicative of the magnitude of the gas or fluid of interest in the ambient environment of the sensor.

42. A dual cavity gas/fluid sensor of claim 41, further comprising a radiation filter formed on said topcap.

43. A differential gas/fluid sensor comprising:

a first wafer;

a first array of thermal sensors formed on said first wafer;

a second array of thermal sensors formed on said second wafer;

a topcap formed on said wafer so as to form a cavity encompassing said first and second arrays of thermal sensors, wherein the cavity can receive gas or fluid from the ambient environment of the sensor;

a first radiation filter situated on said topcap for passing radiation having a first wavelength into the cavity in a first vicinity about said first array of thermal sensors; and a second radiation filter for passing radiation having a second wavelength into the cavity in a second vicinity about said second array of thermal sensors.

44. The sensor of claim 43, further comprising a signal processor for receiving a first signal from said first array of thermal sensors and a second signal from said second array of thermal sensors, and calculating a ratio of the first and second signals to provide an indication of a presence of a gas or fluid in the ambient environment of the sensor.

45. The sensor of claim 44, further comprising a radiation source situated so that radiation can be provided through said first and second filters to the first and second vicinities of said first and second arrays of thermal sensors, respectively.

* * * * *

UNITED STATES PATENT AND TRADEMARK OFFICE
CERTIFICATE OF CORRRECTION

PATENT NO. : 5,852,308  
DATED : December 22, 1998  
INVENTOR(S) : Wood Page 1 of 2

It is certified that error appears in the above-identified patent and that said Letters Patent is hereby corrected as shown below:

On the title page, insert item [56]

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 5 | 1 | 4 | 1 | 3 | 1 | 8/25/92 | Oehler | | | |
| | | 4 | 0 | 4 | 8 | 4 | 9 | 9/13/77 | Kreuzer | | | |
| | | 4 | 8 | 9 | 9 | 0 | 5 | 02/6/90 | Lai | | | |
| | | 4 | 0 | 6 | 7 | 6 | 5 | 1/10/78 | Fletcher | | | |
| | | | | | | | | | | | | |

UNITED STATES PATENT AND TRADEMARK OFFICE
CERTIFICATE OF CORRRECTION

PATENT NO. : 5,852,308
DATED : December 22, 1998
INVENTOR(S) : Wood

It is certified that error appears in the above-identified patent and that said Letters Patent is hereby corrected as shown below:

On the title page, insert item [56]

FOREIGN PATENT DOCUMENTS

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 9 | 6 | 2 | 1 | 1 | 40 | A | 7/11/96 | WO | | | | |
| | | 0 | 7 | 2 | 0 | 0 | 14 | A | 7/3/96 | EP | | | | |
| | | 9 | 5 | 2 | 2 | 0 | 45 | A | 8/17/95 | WO | | | | |
| | | 2 | 9 | 2 | 7 | 4 | 32 | A | 1/24/80 | DE | | | | |
| | | | | | | | | | | | | | | |

Signed and Sealed this

Sixth Day of April, 1999

Attest:

Attesting Officer

Q. TODD DICKINSON

Acting Commissioner of Patents and Trademarks